United States Patent [19]

Martin et al.

[11] 4,410,734
[45] Oct. 18, 1983

[54] OPTICALLY ACTIVE PHENYLPROPANE DERIVATIVES, THEIR PREPARATION AND THEIR USE FOR THE PREPARATION OF FUNGICIDES

[75] Inventors: Christoph Martin, Mannheim; Walter Himmele, Walldorf; Hardo Siegel, Speyer, all of Fed. Rep. of Germany

[73] Assignee: BASF Aktiengesellschaft, Fed. Rep. of Germany

[21] Appl. No.: 213,792

[22] Filed: Dec. 8, 1980

[30] Foreign Application Priority Data

Jan. 16, 1980 [DE] Fed. Rep. of Germany ....... 3001303

[51] Int. Cl.³ ............................................ C07C 33/18
[52] U.S. Cl. .................... 568/715; 560/105; 560/254; 562/492; 562/496; 562/465; 568/643; 568/807
[58] Field of Search ............... 568/715, 807, 808, 592, 568/640, 643; 562/492, 465, 496, 469; 560/55, 59, 102, 105, 254, 255; 260/340.7, 340.9

[56] References Cited

U.S. PATENT DOCUMENTS

| 2,815,381 | 12/1957 | Carpenter et al. | 568/715 |
| 2,815,382 | 12/1957 | Carpenter et al. | 568/715 |
| 3,801,654 | 4/1974 | Seeger et al. | 568/807 |
| 3,830,851 | 8/1974 | David et al. | 568/643 |
| 3,968,168 | 7/1976 | Strong | 568/640 |
| 4,008,270 | 2/1977 | White | 562/496 |
| 4,081,476 | 3/1978 | Anderson et al. | 568/807 |
| 4,144,397 | 3/1979 | Matthews et al. | 562/496 |

FOREIGN PATENT DOCUMENTS

| 1275041 | 8/1968 | Fed. Rep. of Germany | 568/715 |
| 2446046 | 4/1975 | Fed. Rep. of Germany | |
| 2405004 | 8/1975 | Fed. Rep. of Germany | |
| 2750016 | 5/1978 | Fed. Rep. of Germany | |
| 2752135 | 5/1978 | Fed. Rep. of Germany | |
| 2656747 | 6/1978 | Fed. Rep. of Germany | |
| 2752096 | 6/1978 | Fed. Rep. of Germany | |
| 475022 | 11/1937 | United Kingdom | 568/715 |
| 1427097 | 3/1976 | United Kingdom | |

OTHER PUBLICATIONS

Chemistry and Industry (1977), p. 983.
Landury et al., "Chemical Abstracts" vol. 63, (1965) 14891c.
Abe et al., "Chemical Abstracts" vol. 60 (1964) 13175.

Primary Examiner—Werren B. Lone
Attorney, Agent, or Firm—Keil & Witherspoon

[57] ABSTRACT

S-Configurated phenylpropane derivatives of the formula

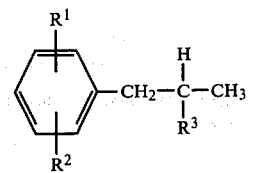

where $R^1$ is alkyl, aryl or alkoxy, $R^2$ is hydrogen, alkyl, aryl or alkoxy, and $R^3$ is carboxyl or esterified carboxyl, acetalized formyl, hydroxymethyl or esterified hydroxymethyl, their preparation by microbiological hydrogenation, and their use for the preparation of fungicidal compounds.

1 Claim, No Drawings

OPTICALLY ACTIVE PHENYLPROPANE DERIVATIVES, THEIR PREPARATION AND THEIR USE FOR THE PREPARATION OF FUNGICIDES

The present invention relates to novel optically active phenylpropane derivatives, their preparation and their use for the preparation of fungicidal compounds.

Fungicidal phenylpropane derivatives have been disclosed (cf. German Laid-Open Applications DOS 2,656,747, DOS 2,750,016 and 2,752,135). 1-[3-(p-tert.-Butylphenyl)-2-methyl]-cis-3,5-dimethylmorpholine I

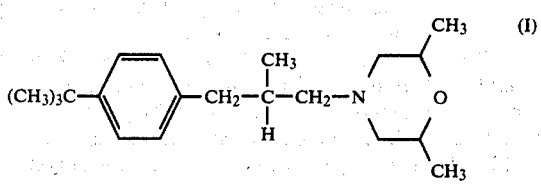

which possesses an asymmetrical carbon atom, has proved particularly active (cf. German Laid-Open Application DOS 2,656,747, claim 3). The (−)-enantiomer of this compound is more active than the racemate. The (−)-enantiomer can be prepared for example by reaction of the racemate I with (+)-camphorsulfonic acid in a diluent, subsequent separation of the diastereomeric salts by fractional crystallization, and reaction of the salt containing the (−)-enantiomer with a strong base (cf. German patent Application P 29 07 614.0, not hitherto laid open, of Feb. 27, 1979). However, this method of enantiomer separation is expensive and furthermore the (+)-enantiomer still present in the mother liquor must be racemized so that it can be reused for enantiomer separation.

We have found that the (−)-enantiomer can be synthesized in a simple manner, starting from a corresponding optically active intermediate, without the undesired (+)-enantiomer being formed at the same time.

The present invention relates to S-configurated phenylpropane derivatives of the formula II

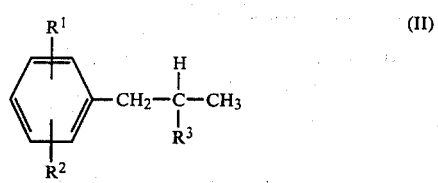

where $R^1$ is alkyl, aryl or alkoxy, $R^2$ is hydrogen, alkyl, aryl or alkoxy, and $R^3$ is carboxyl or esterified carboxyl, acetalized formyl, hydroxymethyl or esterified hydroxymethyl.

Examples of $R^1$ are: as alkyl, an alkyl of 1 to 4 carbon atoms, preferably tert.-butyl; as aryl, phenyl; as alkoxy, an alkoxy of 1 to 4 carbon atoms, preferably tert.-butoxy.

$R^2$ is preferably hydrogen and $R^3$ is preferably formyl, formyl-dimethylacetal, formyl-ethylene glycol acetal, formyl-neopentyl glycol acetal or acetoxymethyl.

The invention further relates to a process for the preparation of the (S)-compounds of the formula II, wherein a compound of the formula III

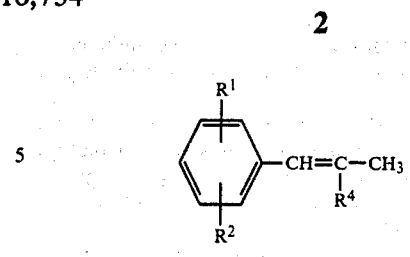

where $R^1$ and $R^2$ have the same meanings as above and $R^4$ is CHO or has the same meanings as $R^3$, is hydrogenated microbiologically.

The microbiological hydrogenation may be carried out with aerobic or facultatively aerobic micro-organisms. A particularly suitable micro-organism is Saccharomyces cerevisiae (pressed yeast, brewer's yeast or baker's yeast). Others which may be used include yeasts of the genera Candida, Rhodotorula and Torulopsis, fungi of the genera Absidia, Aspergillus, Curvularia, Cylindrocarpon, Mucor, Penicillium, Rhizopus, Phycomyces, Geotrichum, Gibberella and Gliocladium, and bacteria of the genera Bacillus, Micrococcus, Mycobacterium, Pediococcus, Proactinomyces, Propionibacterium, Pseudonomas, Serratia, Streptococcus and Streptomyces.

These micro-organisms can easily be isolated in a conventional manner from samples of soil or water.

The micro-organism can be cultured before use in the microbiological hydrogenation; as a rule, such culture is carried out in a conventional manner in an aqueous medium, with the aid of the conventional nutrients. At times it is advantageous to use the culture medium in the hydrogenation step, though the composition of the medium in this step can be substantially simpler.

The microbiological hydrogenation can be carried out, without further additives, solely with the educt (starting material) and the micro-organism. However, it is advantageous to add to the aqueous medium an assimilable carbon source as the nutrient (for example in the form of a sugar), preferably in a concentration of 10–100 g per liter, so that the micro-organism remains active for as long as possible. The addition of a nitrogen source is not necessary; if desired, however, an assimilable nitrogen source can be added, preferably in an amount of about 1–50 g per liter. The fermentation medium can also contain inorganic salts and other growth-promoting substances, such as vitamins.

The pH of the fermentation should preferably be from 2 to 10, especially from 3 to 8, and this range is in most cases attainable without special additives. The temperature may vary within a wide range, for example from 10° C. to 40° C., the range of 20°–35° C. being preferred. To achieve optimum yields, it is advantageous to employ a concentration of 0.1–5% of the educt in the fermentation broth. When the reduction has taken place, further educt can be added. This process can be repeated until the micro-organisms have become inactivated.

The fermentation time depends on the microorganism used and varies from 5 to 200 hours; if educt is added repeatedly, the fermentation time can be correspondingly longer.

The fermentation is preferably carried out aerobically, for example whilst stirring or shaking in the presence of air, or using an aerating apparatus. Preferably, a micro-organism which is in a non-growing (stationary) phase is used. Not only freshly prepared cell mass, but also dried or lyophilized cells, may be used. If an aldehyde group ($R^4$=CHO) is present, it is also reduced, to the hydroxymethyl group, during the microbiological hydrogenation.

The smooth hydrogenation of substituted cinnamaldehydes is surprising, since unsaturated methylphenylpropane derivatives are normally completely inert to microbial attack, or undergo decarboxylation (cf. Chem. Abstr. 91, 290; 35,422 u.).

The compounds II can be converted to the corresponding tosylates or halogen derivatives, which on reaction with an amine give the corresponding amine derivative, eg., with cisdimethylmorpholine, give a compound of the formula IV

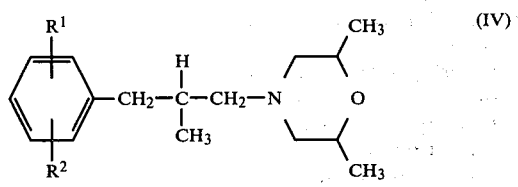

where $R^1$ and $R^2$ have the stated meanings; such compounds are highly active fungicides (cf. German Laid-Open Applications DOS 2,656,747 and 2,752,096).

EXAMPLE 1
(S)-3-(p-tert.-Butylphenyl)-2-methyl-propan-1-ol

A clean but non-sterilized fermenter of 6 liters total volume is charged with the following:

| | |
|---|---|
| fully demineralized water | 1.8 l |
| sucrose | 90 g |
| pressed yeast (Deutsche Hefewerke) | 200 g |
| 3-(p-tert.-butylphenyl)-2-methyl-prop-2-en-1-al | 8 g in 30 ml of ethanol |
| silicone anti-foam agent: | 2 g |
| The fermentation conditions are as follows: | |
| temperature: | 30° C. |
| stirrer speed: | 500 rpm |
| aeration rate: | 1 VVM (volume of air per volume of culture liquid per minute) |
| fermentation time: | 52.5 h |

The fermentation is stopped after 52.5 hours. The cell mass is separated from the nutrient solution by centrifuging; the two phases are each extracted 3 times with methylene chloride. The combined extracts are dried over $Na_2SO_4$ and concentrated by evaporation under reduced pressure. The residue is distilled. Yield of (S)-3-(p-tert.-butylphenyl)-2-methylpropan-1-ol: 4.1 g (51%). $[\alpha]_D^{20} = -7.54°$.

The yield can be increased by optimizing the conditions. The optical purity of the product is determined by NMR in the presence of chiral shift reagents, eg. (Eu(hfbc)₃). The product consists of only one enantiomer. The S-configuration of the microbial product is confirmed by converting the product to (S)-1-[3-(p-tert.-butylphenyl)-2-methyl-propyl]-cis-3,5-dimethylmorpholine.

EXAMPLE 2 2-Methylcinnamyl alcohol derivatives

A round flask, kept at 30° C., is charged with 300 ml of fully demineralized water, 50 g of sucrose and 30 g of dry yeast (Deutsche Hefewerke).

The batch is stirred at 300 rpm. After a fermentation time of 15 minutes, 1.5 g of substrate are added and the mixture is incubated for a further 24 hours. The total culture broth is then extracted 3 times with methylene chloride. The organic phase is dried over $Na_2SO_4$ and concentrated under reduced pressure.

The following products are obtained:

| Educt | Product |
|---|---|
| Ph-CH=C(CH₃)-CHO | Ph-CH₂-CH(CH₃)-CH₂OH  28% |
| tBuO-C₆H₄-CH=C(CH₃)-CHO | tBuO-C₆H₄-CH₂-CH(CH₃)-CH₂OH  93% |
| CH₃O-C₆H₄-CH=C(CH₃)-CHO | CH₃O-C₆H₄-CH₂-CH(CH₃)-CH₂OH  82% |
| CH₃O-(OCH₃)C₆H₃-CH=C(CH₃)-CHO | CH₃O-(OCH₃)C₆H₃-CH₂-CH(CH₃)-CH₂OH  91% |

We claim:
1. (S)-3-(p-tert.-Butylphenyl)-2-methyl-propanol.

* * * * *